(12) United States Patent
King et al.

(10) Patent No.: US 10,315,971 B2
(45) Date of Patent: Jun. 11, 2019

(54) PROCESS FOR RECOVERING HEAT FROM A HYDROCARBON SEPARATION

(71) Applicant: UOP LLC, Des Plaines, IL (US)

(72) Inventors: Stephen T. King, Villa Park, IL (US); Michael R. Van de Cotte, Palatine, IL (US); Adam J. Kanyuh, Streamwood, IL (US); Steven C. Kozup, Chicago, IL (US)

(73) Assignee: UOP LLC, Des Plaines, IL (US)

( * ) Notice: Subject to any disclaimer, the term of this patent is extended or adjusted under 35 U.S.C. 154(b) by 86 days.

(21) Appl. No.: 15/814,288

(22) Filed: Nov. 15, 2017

(65) Prior Publication Data

US 2018/0185766 A1 Jul. 5, 2018

Related U.S. Application Data

(60) Provisional application No. 62/440,111, filed on Dec. 29, 2016.

(51) Int. Cl.
*C07C 7/04* (2006.01)
*C07C 7/09* (2006.01)
(Continued)

(52) U.S. Cl.
CPC ............ *C07C 7/005* (2013.01); *B01D 1/2809* (2013.01); *B01D 1/2812* (2013.01);
(Continued)

(58) Field of Classification Search
CPC .. C07C 7/005; C07C 7/04; C07C 7/09; B01D 1/28; B01D 1/2812; B01D 1/2843;
(Continued)

(56) References Cited

U.S. PATENT DOCUMENTS 4,121,917 A * 10/1978 Baker .................... C07C 7/005
62/50.2
4,634,799 A 1/1987 Haun et al.
(Continued)

FOREIGN PATENT DOCUMENTS

EP 0728284 A1 8/1996
WO 2016053668 A1 4/2016

OTHER PUBLICATIONS

Mowery et.al., Efficient, High Recovery of Liquids From Natural Gas Utilizing a High Pressure Absorber, Lummus Process Technology—Randall Gas Technologies Houston, Texas, U.S.A.
(Continued)

*Primary Examiner* — Renee Robinson (57) ABSTRACT

Systems and processes for heat recovery associated with the separation of hydrocarbon components. Two compressors are used to compress a portion of an overhead vapor stream from a fractionation column. A pressure of the liquid portion of the compressed overhead is reduced and used to recover heat from an overhead of another separation zone having a fractionation column. Once the heat has been recovered the stream is recompressed. The recovered heat may be removed from the recompressed stream in a reboiler of another fractionation column. The fractionation columns may comprise a deethanizer stripper, propane-propylene splitter, and a depropanizer column.

18 Claims, 2 Drawing Sheets

(51) Int. Cl.

| | | |
|---|---|---|
| *B01D 1/28* | (2006.01) | |
| *C07C 7/00* | (2006.01) | |
| *B01D 3/14* | (2006.01) | |
| *B01D 3/42* | (2006.01) | |
| *C07C 11/06* | (2006.01) | |

(52) U.S. Cl.
CPC ......... *B01D 1/2843* (2013.01); *B01D 1/2846* (2013.01); *B01D 1/2856* (2013.01); *B01D 1/2881* (2013.01); *B01D 1/2884* (2013.01); *B01D 3/141* (2013.01); *B01D 3/143* (2013.01); *B01D 3/4227* (2013.01); *C07C 7/04* (2013.01); *C07C 7/09* (2013.01); *C07C 11/06* (2013.01); *Y02P 20/123* (2015.11); *Y02P 20/124* (2015.11); *Y02P 20/51* (2015.11); *Y02P 20/57* (2015.11); *Y02P 70/34* (2015.11)

(58) Field of Classification Search
CPC .. B01D 1/2846; B01D 1/2856; B01D 1/2884; B01D 3/14; B01D 3/143
See application file for complete search history.

(56) References Cited

U.S. PATENT DOCUMENTS

| | | |
|---|---|---|
| 5,110,446 A | 5/1992 | Harandi et al. |
| 5,673,571 A | 10/1997 | Manley |
| 6,864,401 B2 | 3/2005 | Van Egmond |
| 7,687,677 B1 | 3/2010 | O'Brien et al. |
| 7,981,256 B2 | 7/2011 | Wegerer et al. |
| 8,349,263 B2 | 1/2013 | Panditrao |
| 9,079,810 B2 | 7/2015 | Gartside et al. |
| 9,334,204 B1 | 5/2016 | Radaelli et al. |
| 9,352,295 B2 | 5/2016 | Rafique et al. |
| 2006/0004242 A1* | 1/2006 | Verma .................... C07C 7/005 585/809 |
| 2013/0131417 A1 | 5/2013 | Werba et al. |
| 2015/0052940 A1 | 2/2015 | King et al. |
| 2015/0101921 A1 | 4/2015 | King et al. |

OTHER PUBLICATIONS

CB&I Proprietary Randall Gas HPA (http://www.cbi.com/getattachment/488f3aec-df36-4a40-abec-d35bd9575441/HPA-SM.aspx). Chicago Bridge & Iron Company.

Huebel et al., New NGL-recovery process provides viable alternative (http://www.cbi.com/getattachment/81764aaa-9fed-472f-9e55-7cbd63d3938f/New-NGL-recovery-process-provides-viable.aspx).

PCT Search Report dated Feb. 7, 2018 for corresponding PCT Application No. PCT/US2017/055856.

* cited by examiner

PROCESS FOR RECOVERING HEAT FROM A HYDROCARBON SEPARATION

CROSS-REFERENCE TO RELATED APPLICATION

This application claims priority from Provisional Application No. 62/440,111 filed Dec. 29, 2016, the contents of which cited application are hereby incorporated by reference in its entirety.

FIELD OF THE INVENTION

This invention relates generally to processes and systems associated with recovering heat from a hydrocarbon separation process.

BACKGROUND OF THE INVENTION

Petroleum refining and petrochemical processes frequently involve separating hydrocarbon components that have very similar structure and properties.

For example, propylene-propane splitters typically comprise distillation towers that are used to separate hydrocarbons streams into polymer grade propylene (PGP) stream as a net overhead stream and a stream with propane in a net bottoms. Due to the low relative volatility of propylene and propane, typically a very large tower with 150 to 250 trays is used. Additionally, the tower also typically requires a reflux to feed ratio of 5 to 10 to make the separation. Since the relative volatility of propylene and propane is so low (typically 1.05 to 1.20), the fractionation is energy intensive in order to separate propylene and propane into high purity component streams.

Typically, a heat pump compressor is utilized to condense (or remove energy) in the fractionation column overhead and re-boil (or feed energy) into the column bottoms because the vapor pressure of propylene and propane are similar and the heat removed from the column overhead for condensing can be transferred or pumped to the tower bottoms for re-boiling.

In some designs, such as the design disclosed in U.S. Pat. Pub. No. 2013/0131417, which is assigned to the Assignee of the present invention, and the entirety of which is incorporated herein by reference, an overhead vapor from a propylene-propane splitter column ("PP Splitter") is sent to the first stage heat pump compressor. The stream being separated in the PP Splitter is typically from an upstream deethanizer. In the first stage heat pump compressor, the overhead vapor of the PP Splitter is compressed to the required pressure, typically between approximately 1,034 to 1,724 kPag (150 to 250 psig), which is the minimum temperature for a heat exchanger to condense vapor on the hot side and re-boil liquid on the cold side of the heat exchanger. The duty required to re-boil the PP Splitter determines the vapor flow rate to the re-boiler/condensers. Since the condensing duty is greater than the re-boiling duty of PP Splitter, there is excess vapor from the first stage discharge that requires condensation. This extra vapor is sent to the second stage of the heat pump compressor, where it can be compressed to a pressure able to be condensed by another heat exchanger at a warmer temperature. Subsequently, this stream is flashed across a valve into a suction drum down to the column overhead pressure to provide Joule-Thomson effect cooling to the column overhead and accumulate propylene liquid product in the suction drum. In such a system described above, when the second stage discharge stream is flashed down to the column overhead pressure, the resulting vapor from this flash is then reprocessed in the heat pump first stage and second stages, sequentially. Thus, the first stage of the heat pump compressor, which is the larger capacity stage requiring more utility, needs to process the column overhead vapor along with the vapor from the second stage discharge flash, thereby increasing the overall capacity and utility requirement of the compressor.

Another system for recovering heat from a PP Splitter is disclosed in U.S. Pat. No. 7,981,256, which is also assigned to the Assignee of the present invention, and the entirety of which is incorporated herein by reference. In the design depicted in U.S. Pat. No. 7,981,256, a multi-stage heat compressor system is used to transfer heat from the overhead stream of the PP Splitter to reboilers for the PP Splitter. This application utilizes at least three stages and still requires an external refrigeration system for the upstream deethanizer.

In yet another design is disclosed in U.S. Pat. Pub. No. 2015/0101921, assigned to the Applicant of the present application, and the entirety of which is incorporated herein by referenced, utilizes a single, 2-stage compressor. The system and processes disclosed in U.S. Pat. Pub. No. 2015/0101921 recognize that the refrigeration system needed to condense the deethanizer rectifier is often expensive. However, the heat removed for the PP Splitter overhead condensation is wasted with air or cooling water.

While these designs are presumably effective for their intended purposes, there is a continuing need to develop and provide processes which improve on energy efficiency and heat recovery.

SUMMARY OF THE INVENTION

Systems and processes which allow for more efficient heat recovery associated with the separation of hydrocarbons have been discovered which utilize a single stage heat pump compressor and a multi-stage heat recovery compressor. The present configurations utilize liquid from the heat recovery compressor second stage suction drum to condense the deethanizer. Additionally, liquid from the heat recovery second stage suction drum is pumped out to storage as net propylene liquid product (the column net overhead product). The propylene trim cooler may be utilized to sub-cool liquid from the depropanizer reboiler outlet which is flashed back to the heat recovery second stage suction drum. It is contemplated that the additional heat contained in the stream is used to reboil a downstream depropanizer column.

In the present configurations, the vapor from the PP Splitter column overhead is processed in the single stage heat pump compressor. The heat pump compressor is preferably a centrifugal type compressor with anti-surge control. A heat pump compressor suction drum is provided since the column overhead very tall and the distance between the column overhead and compressor suction is very long and could result in high residence time and greater chance of ambient heat loss. A separate multi-stage heat recovery compressor is used for recovering heat from the deethanizer overhead and PP Splitter overhead and transferring it to the depropanizer for reboiling. The heat recovery compressor is also a centrifugal type compressor with anti-surge control. It is preferred that the heat pump compressor and heat recovery compressor are separate machines because the vapor flowrate of the heat pump compressor is more than ten times the volume flow of the heat recovery compressor. Additionally, having separate machines allows the flexibility to adjust the duty of the deethanizer overhead condenser without changing the duty of the PP Splitter Reboiler, thus keeping the columns independent.

In the present processes and systems, the PP Splitter overhead pressure is controlled by regulating heat recovery compressor flowrate. More flow rate though the heat recovery compressor will allow more duty extracted by the depropanizer upper reboiler and propylene trim cooler. This provides better control of the column overhead pressure. Additionally, the deethanizer off-gas exchanger is used to sub-cool the deethanizer stripper reflux to reduce the vapor load in the deethanizer rectifier and reduce the rectifier condenser duty and stripper condenser duty. Finally, the temperature of the deethanizer rectifier condenser is controlled by regulating the heat recovery first stage suction drum pressure. Also, the heat removed from the deethanizer overhead can be used to reboil the depropanizer. In previous designs, this heat was dissipated to air or cooling water.

Accordingly, in one aspect, the present invention may be characterized as a process for separating hydrocarbons and recovering heat comprising separating a stream comprising C4– hydrocarbons in a first separation zone into an overhead stream and a C3+ bottoms stream; separating the C3+ bottoms stream in a second separation zone into a propylene overhead stream and a bottoms stream comprising propane; compressing the propylene overhead stream in a first compression zone configured to provide a compressed propylene overhead stream; recovering heat from a first portion of the compressed propylene overhead stream in a heat exchange zone associated with the second separation zone; condensing a second portion of the compressed propylene overhead stream in a separation vessel, the separation vessel providing a propylene vapor stream and a propylene liquid stream; reducing a pressure of at least a portion of the propylene liquid stream to provide a reduced pressure stream; recovering heat with the reduced pressure steam in a second heat exchange zone, the second heat exchange zone associated with the first separation zone and being configured to condense a portion of the overhead stream and provide a vaporized propylene stream; compressing the vaporized propylene stream in a second compression zone configured to provide a re-compressed propylene stream; and, mixing the re-compressed propylene stream with the second portion of the compressed propylene overhead stream in the separation vessel.

Accordingly, in another aspect, the present invention may be characterized as a process for separating hydrocarbons and recovering heat comprising separating a stream comprising in a first separation zone configured to separate the stream into an overhead stream and a C3+ bottoms stream; passing the C3+ bottoms stream to a second separation zone configured to separate the C3+ bottoms stream and provide a propylene overhead stream and a bottoms stream, the bottom stream including propane; passing the bottoms stream of the second separation zone to a third separation zone; passing the propylene overhead stream to a first compression zone configured to compress the propylene overhead stream and provide a compressed propylene overhead stream; passing a first portion of the compressed propylene overhead stream to a heat exchange zone associated with the second separation zone configured to remove heat from the first portion of the compressed propylene overhead stream; passing a second portion of the compressed propylene overhead stream to a separation vessel configured to allow the second portion of the compressed propylene overhead stream to be cooled and separate into a vapor propylene stream and a liquid propylene stream; reducing a pressure of at least a portion of the liquid propylene stream to provide a reduced pressure stream, the reduced pressure stream comprising a mixture of liquid and vapor; passing the reduced pressure stream to a second heat exchange zone associated with the first separation zone and configured to vaporize liquid in the reduced pressure stream and provide a vaporized propylene stream, wherein the second heat exchange zone also receives a portion of the overhead stream from the first separation zone; passing the vaporized propylene stream to a second compression zone configured to compress the vaporized propylene stream and provide a re-compressed propylene stream; and, passing the re-compressed propylene stream to the separation vessel.

In still another aspect, the present invention may be characterized as a system for separating hydrocarbons and recovering heat comprising a first separation zone comprising a fractionation column configured to receive and separate a stream into an overhead stream and a C3+ bottoms stream; a second separation zone comprising a fractionation column configured to receive and separate the C3+ bottoms stream and provide a propylene overhead stream and a bottoms stream, the bottom stream comprising propane; a first compression zone configured to compress the propylene overhead stream and provide a compressed propylene overhead stream; a heat exchange zone associated with the second separation zone and configured to remove heat from the first portion of the compressed propylene overhead stream; a separation vessel configured to receive and separate a second portion of the compressed propylene overhead stream into a vapor propylene stream and a liquid propylene stream; a valve configured to receive a portion of the liquid propylene stream and provide a reduced pressure stream; a second heat exchange zone, the second heat exchange zone associated with the first separation zone and configured to heat the reduced pressure portion and provide a vaporized propylene stream; a second compression zone configured to compress the reduced pressure stream and the vapor propylene stream and provide a re-compressed propylene stream; and, one or more lines configured to pass the re-compressed propylene stream to the separation vessel.

Additional aspects, objects, embodiments, and details of the invention are set forth in the following detailed description of the invention.

DEFINITIONS

As depicted, process flow lines in the figures can be referred to, interchangeably, as, e.g., lines, pipes, branches, distributors, streams, effluents, feeds, products, portions, catalysts, withdrawals, recycles, suctions, discharges, and caustics.

As used herein, the term "zone" can refer to an area including one or more equipment items and/or one or more sub-zones. Equipment items can include one or more reactors or reactor vessels, heaters, exchangers, pipes, pumps, compressors, and controllers. Additionally, an equipment item, such as a reactor, dryer, or vessel, can further include one or more zones or sub-zones.

As used herein, the term "vapor" can mean a gas or a dispersion that may include or consist of one or more hydrocarbons.

As used herein, the term "stream" can include various hydrocarbon molecules and other substances. Moreover, the term "stream comprising Cx hydrocarbons" or "stream comprising Cx olefins" can include a stream comprising hydrocarbon or olefin molecules, respectively, with "x" number of carbon atoms, suitably a stream with a majority of hydrocarbons or olefins, respectively, with "x" number of carbon atoms and preferably a stream with at least 75 wt-% hydrocarbon molecules, respectively, with "x" number of carbon atoms. Moreover, the term "stream comprising Cx+ hydrocarbons" or "stream comprising Cx+ olefins" can include a stream comprising a majority of hydrocarbon or olefin molecules, respectively, with more than or equal to "x" carbon atoms and suitably less than 10 wt-% and preferably less than 1 wt-% hydrocarbon or olefin molecules, respectively, with x−1 carbon atoms. Lastly, the term "Cx− stream" can include a stream comprising a majority of hydrocarbon or olefin molecules, respectively, with less than or equal to "x" carbon atoms and suitably less than 10 wt-% and preferably less than 1 wt-% hydrocarbon or olefin molecules, respectively, with x+1 carbon atoms.

As used herein, the term "overhead stream" can mean a stream withdrawn at or near a top of a vessel, such as a column.

The term "column" means a distillation column or columns for separating one or more components of different volatilities. Unless otherwise indicated, each column includes a condenser on an overhead of the column to condense the overhead vapor and reflux a portion of an overhead stream back to the top of the column. Also included is a reboiler at a bottom of the column to vaporize and send a portion of a bottom stream back to the bottom of the column to supply fractionation energy. Feeds to the columns may be preheated. The top pressure is the pressure of the overhead vapor at the outlet of the column. The bottom temperature is the liquid bottom outlet temperature. Overhead lines and bottom lines refer to the net lines from the column downstream of the reflux or reboil to the column.

As used herein, the term "bottom stream" can mean a stream withdrawn at or near a bottom of a vessel, such as a column.

DETAILED DESCRIPTION OF THE INVENTION

A method has been developed which allows for a more efficient separation of various hydrocarbons by increasing the heat recovery from same. In a specific application of the present invention, the innovation is used in associated with a deethanizer and a PP splitter. The deethanizer requires a refrigerated condensing system to recover the C3 material and reject the C2− material as vapor. The separation is performed at high pressure (approximately 2,758 kPag (400 psig)) to keep the material in liquid phase in the overhead receiver. The deethanizer refrigeration system is typically a skid mounted system consisting of a 2-stage compressor, two disengaging drums, accumulator, and cooler (air cooled or water cooled exchanger). Typically, this is an extra unit to be purchased, which may add to the overall capex and complexity of the system increasing the plant equipment count. Additionally, typically these refrigeration units can utilize oil flooded screw compressors for some catalytic dehydrogenation units processing less than 500 kmta (one-thousand metric tons per year). These screw compressors are typically not as reliable as centrifugal compressors.

Accordingly, the present processes and systems utilize the PP Splitter overhead system to condense the deethanizer rectifier overhead instead of using a separate modular skid refrigeration unit. The refrigeration unit commonly uses propylene as refrigerant which is available in the PP Splitter overhead. For this integrated scheme, two compressors are preferred: a heat pump compressor used to reboil the PP splitter and condense the primary reflux material for the PP splitter; and a heat recovery compressor that condenses the PP splitter secondary reflux and net overhead material and also condenses the deethanizer rectifier overhead material. It is desirable to have these compressors separate machines because the vapor flowrate to the heat pump compressor is much greater than the vapor flowrate to the heat recovery compressor. Additionally, the use of separate compressors provides better control if the duty of the deethanizer needs to be adjusted without the PP Splitter being impacted.

The heat from the condensation of these two columns can be recovered and transferred to a depropanizer as reboiling heat. The extraction of heat from the deethanizer rectifier overhead allows more heat to be transferred to the depropanizer heat recovery reboiler to reduce the LP steam consumption of the depropanizer. This is believed to result in a significant utility reduction as well as a reduction in capital costs. These and other benefits will be appreciated in view of the follow description of some of the embodiments of the present invention.

Figure 1:
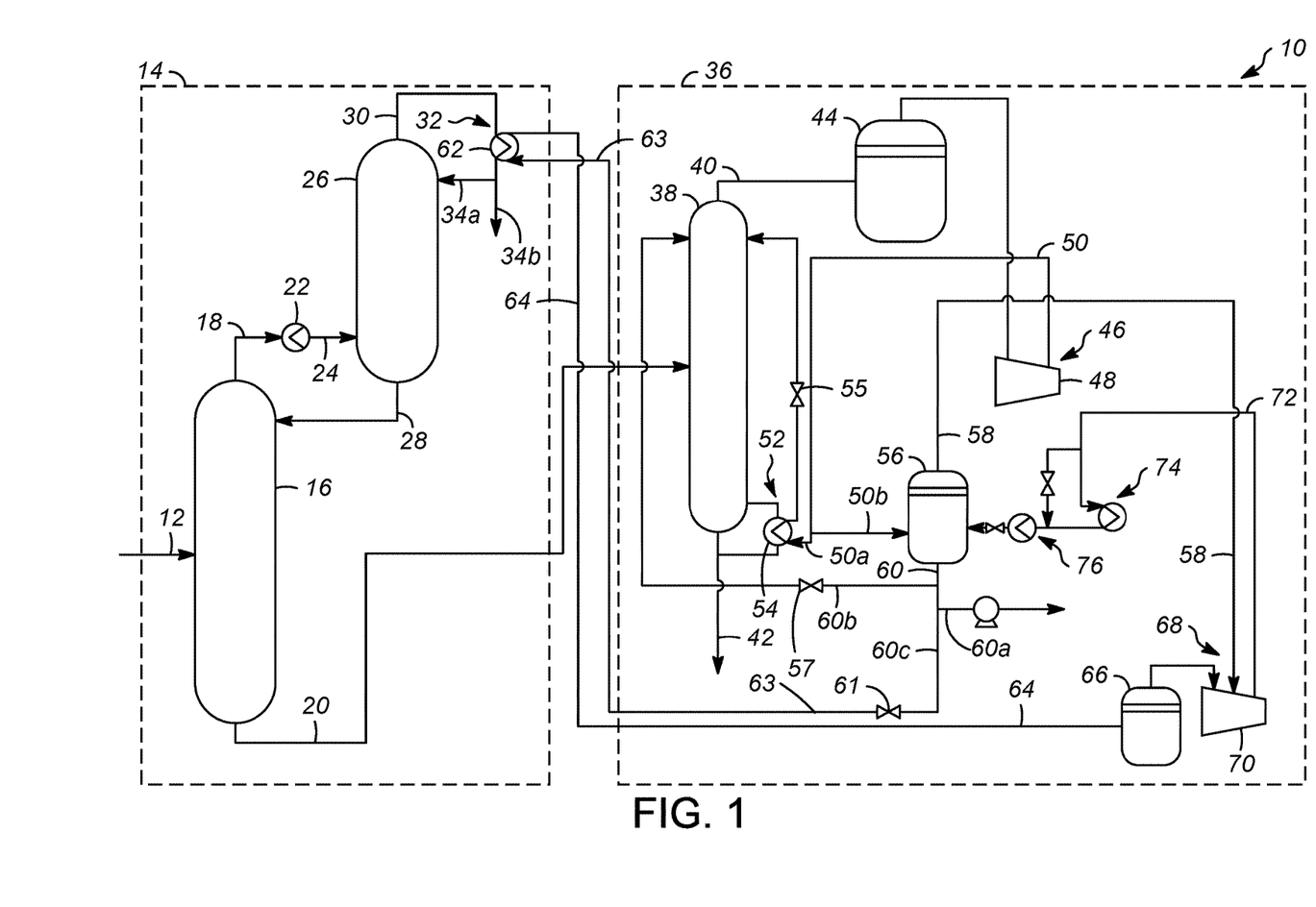
FIG. 1 depicts a system and process flow diagram of a process according to one or more embodiments of the present invention.

With reference to FIG. 1, the present invention will be described, with reference to a system generally designated 10. As shown, a feed stream 12 comprising hydrocarbons to be separated is passed to a first separation zone 14. The feed stream 12 may comprise a liquid effluent from, for example, a cryogenic separation unit, and which comprises C4− hydrocarbons.

In a preferred embodiment, the first separation zone 14 comprises at least one fractionation column 16 for separating hydrocarbons in the feed steam 12 based upon boiling point. In a most preferred embodiment, the fractionation column 16 in the first separation zone 14 comprises a deethanizer stripping column (or deethanizer stripper). The purpose of section 14 is to remove the C2− hydrocarbons and lighter material from the C3+ hydrocarbons.

As is known, the fractionation column 16, such as the deethanizer stripping column, are operated under conditions to separate the hydrocarbons in the feed stream 12 into an overhead vapor stream 18 and a bottoms stream 20. In at least one embodiment, the fractionation column 16 is operated with an overhead pressure of approximately 2,930 kPag (425 psig). From a deethanizer stripping column, the bottoms stream 20 will comprise C3+ hydrocarbons, and the overhead vapor stream 18 will comprise mostly C2− hydrocarbons, but will likely include some C3+ hydrocarbons.

Accordingly, in order to recover some of the heavier hydrocarbons from the overhead vapor stream 18, the overhead vapor stream 18 may be cooled with, for example, cooling water (or air cooling) in a heat exchanger 22 to provide a partially condensed overhead stream 24. The partially condensed stream 24 is passed to another fractionation column 26 in the first separation zone 14, for example a deethanizer rectifier, in which the components of the partially condensed stream 24 can disengage into a liquid and a vapor phase in the bottom of the second fractionation column 26. The vapor will get further fractionated in the second fractionation column 26 where the C2− material will be removed from the C3 material. An overhead liquid stream 28 from the second fractionation column 26 can be passed back to the first fractionation column 16 as a reflux to the stripping column. A vapor stream 30 from the second fractionation column 26 is condensed in a heat exchange zone 32 where a liquid stream 34a (containing C3 hydrocarbons) can be refluxed back to the second fractionation column 26, while an off-gas stream 34b, comprising C2− and lighter components, may be processed further.

It is desirable to utilize a two-column system for the first separation zone 14 with an air or water cooler in between (at heat exchanger 22) to reduce the refrigeration duty required for the heat exchange zone 32 for the vapor stream 30. However, a design with a single column incorporating both fractionation columns 26, 16 together with no intercooling at the heat exchanger 22 is also contemplated. In a single column system for the first separation zone 14 with no intercooling, the required refrigeration duty of the heat exchange zone 32 would be greater. Since refrigeration duty is typically more expensive than air or water cooling, it may be economically desirable to utilize the two-column system for the first separation zone 14 as depicted.

As discussed at the outset above, typically the heat exchange zone 32 utilizes a refrigerated condensing system on the vapor stream 30 from the second fractionation column 26 and a vapor/liquid disengaging drum. In the present processes and systems, the condensation of the vapor stream 30 from the second fractionation column 26 is accomplished with a separate refrigeration unit using propylene or lighter as a heat exchange medium.

More specifically, returning to the fractionation column 16, the bottoms stream 20 from the first separation zone 14 is passed to a second separation zone 36. The second separation zone 36 comprises at least one fractionation column 38 for separating hydrocarbons in the bottoms stream 20 from the fractionation column 16 in the first separation zone 14 based upon relative volatility. In a most preferred embodiment, the fractionation column 38 in the second separation zone 36 comprises a propylene-propane splitter column to produce polymer grade propylene in the net overhead and propane in the net bottoms.

As is known, the fractionation column 38 of the second separation zone 36, such as the propylene-propane splitter column, is operated under conditions to separate the hydrocarbons in the bottoms stream 20 from the fractionation column 16 in the first separation zone 14 into another overhead vapor stream 40 and another bottoms stream 42. In at least one embodiment, the fractionation column 38 is operated with an overhead pressure of approximately 689 kPag (100 psig). From a propylene-propane splitter column, the bottoms stream 42 will comprise at least 90 wt % propane and heavier hydrocarbons and the overhead vapor stream 40 will comprise a propylene overhead stream. The bottoms stream 42 from the second separation zone 36 may be passed to another separation zone 100 (see, FIG. 2) which may comprise a depropanizer column 102, discussed in more detail below.

The remaining portions of the description will relate to an embodiment in which the fractionation column 38 in the second separation zone 36 comprises a PP Splitter; however, such is not intended to be limiting.

The overhead vapor stream 40 or propylene overhead stream from the fractionation column 38 in the second separation zone 36 is passed to a liquid knockout drum 44, and then to a first compression zone 46. The first compression zone 46 includes a single stage heat pump compressor 48 that produces an output that includes mostly propylene and comprises a compressed propylene stream 50. The heat pump compressor 48 will compress the overhead vapor stream 40 from the fractionation column 38 in the second separation zone 36 up to approximately 1,207 kPag (175 psig) to form the compressed propylene stream 50.

The compressed propylene stream 50 is split into at least two portions 50a, 50b with approximately 75 to 90% (e.g., the first portion 50a) being passed a heat exchange zone 52 to recover and transfer heat (or heat pump) from the compressed propylene stream 50. More specifically, the heat from the hot side of a heat exchanger 54 in the heat exchange zone 52 transfers to the cold side and serves as a heat source to re-boil the fractionation column 38 in the second separation zone 36. The heat exchanger 54, as well as other heat exchangers discussed herein, may be also of any conventional design, with one example being a cross-flow (TEMA X shell) shell-in-tube design and another example using high heat transfer technologies such as Highflux™ (available from UOP, Des Plaines, Ill.) or plate type exchangers. The vapor in the hot side outlet of the heat exchanger 54 fully condenses and is passed back to the fractionation column 38 in the second separation zone 36 as primary reflux material. The outlet of the heat exchanger 54 may include a 34 to 172 kPa (5 to 25 psi) pressure drop, via a valve 55, for controlling the flow of first portion 50a of the compressed propylene stream 50 back to the fractionation column 38 in the second first separation zone 36.

The second portion 50b of the compressed propylene stream 50 (preferably the remaining 10 to 25%) bypasses the heat exchange zone 52 and is passed to a separation vessel 56, preferably comprising a second stage suction drum, having an operating pressure of approximately 1,241 kPag (175 psig). In the separation vessel 56, the compressed propylene stream 50 will be cooled by, for example, contact with another stream (discussed below), resulting in a portion of the vapor in the separation vessel 56 condensing. Thus, the separation vessel 56 will provides a vapor propylene stream 58 and a liquid propylene stream 60.

A portion 60a of the liquid propylene stream 60 may be recovered (as the net overhead product). Additionally, another portion 60b of the liquid propylene stream 60 may be passed back to the fractionation column 38 in the second separation zone 36 via a line due to the pressure differential between the separation vessel 56 and the overhead pressure of the fractionation column 38 in the second separation zone 36 as secondary reflux. A valve 57 can reduce the pressure of the second portion 60b of the liquid propylene stream 60. A third portion 60c of the liquid propylene stream 60 is flashed down to a lower pressure (between approximately 138 to 345 kPag (20-50 psig)) via, for example, a valve 61 to provide a reduced pressure stream 63 which may then be utilized to recover heat from the first separation zone 14. This will replace the refrigeration unit discussed above.

Returning to FIG. 1, in the depicted processed, the reduced pressure stream 63 is passed from the valve 61 to a heat exchanger 62 to associated with the vapor stream 30 of the first separation zone 14 discussed above. The reduced pressure stream 63 will typically contain a mixture of liquid and vapor. In the heat exchanger 62, the liquid portion of the reduced pressure portion 63 will be vaporized, preferably, in the shell side of a kettle (TEMA K shell) heat exchanger. A vaporized propylene stream 64 can be passed from the heat exchanger 62 to a stage suction drum 66, discussed below. Additionally, as discussed above, in the heat exchange zone 32 having the heat exchanger 62, a portion of the vapor stream 30 will be condensed and passed back in stream 34a to the second fractionation column 26 in the first separation zone 14.

The vaporized propylene stream 64 is passed to the second stage suction drum 66 (with a pressure between approximately 138 to 345 kPag (20-50 psig)), and then to a second compression zone 68 having a heat recovery compressor 70. The heat recovery compressor 70 may also process a portion of the vapor propylene stream 58 from the separation vessel 56. In the heat recovery compressor 70, the vapor streams 58, 64 will be compressed to approximately 2,689 kPag (390 psi). From the heat recovery compressor 70, a re-compressed propylene stream 72 can be returned to the separation vessel 56. However, since the re-compressed propylene stream 72 contains recoverable heat, it is preferred that the heat from the re-compressed propylene stream 72 is recovered first.

For example, the heat from the re-compressed propylene stream 72 may be recovered or removed in a heat exchange zone 74. Preferably, with reference to FIG. 2, the heat exchange zone 74 is associated with a reboiler of a depropanizer column 102. The depropanizer column 102 is typically used to separate the bottoms stream 42 from the fractionation column 36 in the second separation zone 36.

Figure 2:
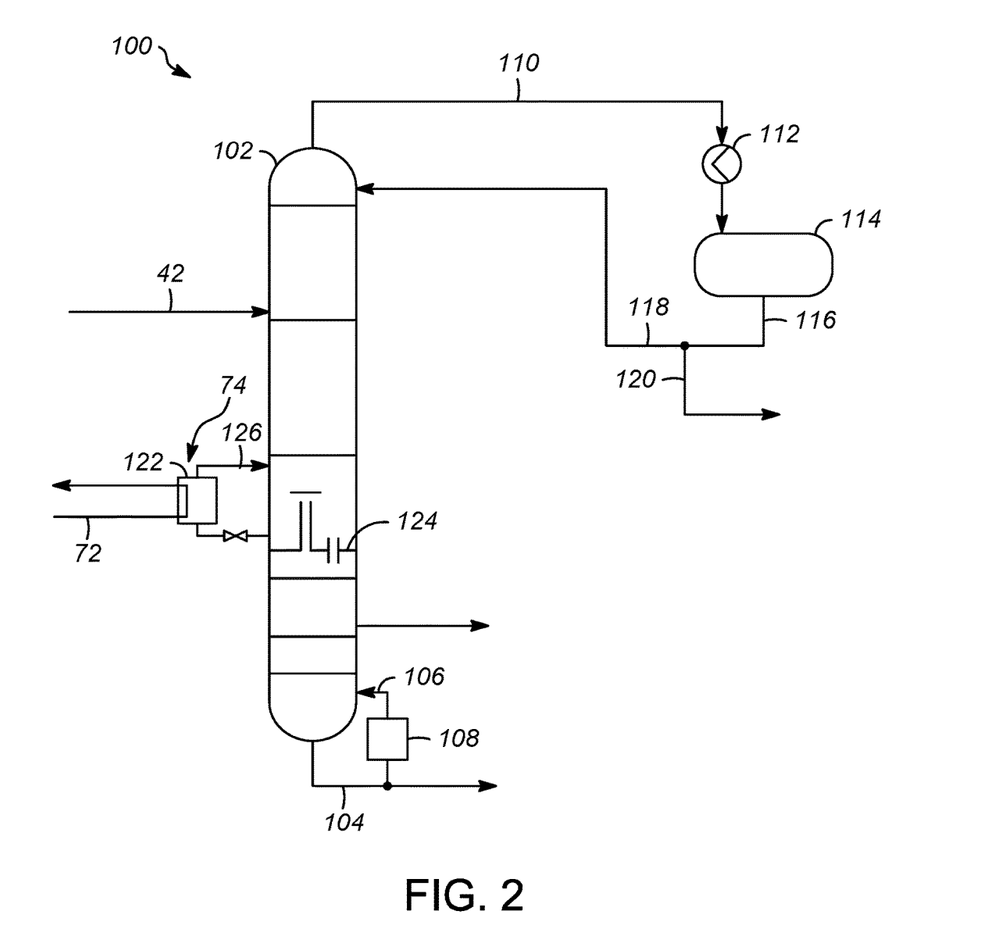
FIG. 2 depicts a portion of a process flow diagram according to one or more embodiments of the present invention.

The depropanizer column 102, which is exemplary, produces a column bottoms stream 104 containing C4+ components and a net overhead stream 120 comprising C3− material. A reboiler return stream 106 is returned to the depropanizer column 102 after it has been vaporized in a steam reboiler 108.

An overhead stream 110 from the depropanizer column 102 is cooled in a heat exchanger 112 and sent to a column overhead receiver 114. A condensed stream 116 is separated into a reflux stream 118 sent to the depropanizer column 102 and a propane stream 120 which may be recovered.

The heat exchange zone 74 which is utilized to recovered heat from the re-compressed propylene stream 72 preferably comprises a reboiler 122 which feeds off a liquid accumulator tray 124. The re-compressed propylene stream 72 is used to heat a recycle stream 126 in the reboiler 122 to provide heat to the depropanizer column 102. This is merely an exemplary configuration.

Returning to FIG. 1, another heat exchange zone 76, for example, one associated with a PP Splitter trim cooler may be used to sub-cool re-compressed propylene stream 72 before the re-compressed propylene stream 72 is passed to the separation vessel 56 as discussed above. The heat exchanger 76 is used to remove residual heat from the process and is typically an air cooled or water cooled exchanger. In the vapor/liquid separation vessel 56, the re-compressed C3 overhead stream 72 will separate as discussed above.

It is believed that processes and systems according to one or more embodiments described herein provide more efficient heat recovery, as well as a savings on the capital required to implement the processes and systems.

It should be appreciated and understood by those of ordinary skill in the art that various other components such as valves, pumps, filters, coolers, etc. were not shown in the drawings as it is believed that the specifics of same are well within the knowledge of those of ordinary skill in the art and a description of same is not necessary for practicing or understating the embodiments of the present invention.

SPECIFIC EMBODIMENTS

While the following is described in conjunction with specific embodiments, it will be understood that this description is intended to illustrate and not limit the scope of the preceding description and the appended claims.

A first embodiment of the invention is a process for separating hydrocarbons and recovering heat comprising separating a stream comprising C4− hydrocarbons in a first separation zone into an overhead stream and a C3+ bottoms stream; separating the C3+ bottoms stream in a second separation zone into a propylene overhead stream and a bottoms stream comprising propane; compressing the propylene overhead stream in a first compression zone configured to provide a compressed propylene overhead stream; recovering heat from a first portion of the compressed propylene overhead stream in a heat exchange zone associated with the second separation zone; condensing a second portion of the compressed propylene overhead stream in a separation vessel, the separation vessel providing a propylene vapor stream and a propylene liquid stream; reducing a pressure of at least a portion of the propylene liquid stream to provide a reduced pressure stream; recovering heat with the reduced pressure steam in a second heat exchange zone, the second heat exchange zone associated with the first separation zone and being configured to condense a portion of the overhead stream and provide a vaporized propylene stream; compressing the vaporized propylene stream in a second compression zone configured to provide a re-compressed propylene stream; and, mixing the re-compressed propylene stream with the second portion of the compressed propylene overhead stream in the separation vessel. An embodiment of the invention is one, any or all of prior embodiments in this paragraph up through the first embodiment in this paragraph further comprising compressing the propylene vapor stream from the separation vessel in the second compression zone. An embodiment of the invention is one, any or all of prior embodiments in this paragraph up through the first embodiment in this paragraph further comprising removing heat from the re-compressed propylene stream before the re-compressed propylene stream is mixed with the second portion of the compressed propylene overhead stream in the separation vessel. An embodiment of the invention is one, any or all of prior embodiments in this paragraph up through the first embodiment in this paragraph wherein the heat is removed from the re-compressed propylene stream in a third heat exchange zone associated with a third separation zone configured to receive the bottoms stream from the second separation zone 36. An embodiment of the invention is one, any or all of prior embodiments in this paragraph up through the first embodiment in this paragraph further comprising separating the first portion of the compressed propylene overhead stream in a fractionation column in the second separation zone. An embodiment of the invention is one, any or all of prior embodiments in this paragraph up through the first embodiment in this paragraph further comprising recovering a second portion of the propylene liquid stream as a propylene product stream. An embodiment of the invention is one, any or all of prior embodiments in this paragraph up through the first embodiment in this paragraph further comprising refluxing a third portion of the propylene liquid stream from the separation vessel to a fractionation column in the second separation zone. An embodiment of the invention is one, any or all of prior embodiments in this paragraph up through the first embodiment in this paragraph wherein the first separation zone comprises two fractionation columns, and wherein the second separation zone comprises a fractionation column. An embodiment of the invention is one, any or all of prior embodiments in this paragraph up through the first embodiment in this paragraph further comprising transferring heat from the re-compressed propylene stream to a third separation zone configured to receive the bottoms stream from the second separation zone.

A second embodiment of the invention is a process for separating hydrocarbons and recovering heat comprising separating a stream comprising in a first separation zone configured to separate the stream into an overhead stream and a C3+ bottoms stream; passing the C3+ bottoms stream to a second separation zone configured to separate the C3+ bottoms stream and provide a propylene overhead stream and a bottoms stream, the bottom stream including propane; passing the bottoms stream of the second separation zone to a third separation zone; passing the propylene overhead stream to a first compression zone configured to compress the propylene overhead stream and provide a compressed propylene overhead stream; passing a first portion of the compressed propylene overhead stream to a heat exchange zone associated with the second separation zone configured to remove heat from the first portion of the compressed propylene overhead stream; passing a second portion of the compressed propylene overhead stream to a separation vessel configured to allow the second portion of the compressed propylene overhead stream to be cooled and separate into a vapor propylene stream and a liquid propylene stream; reducing a pressure of at least a portion of the liquid propylene stream to provide a reduced pressure stream, the reduced pressure stream comprising a mixture of liquid and vapor; passing the reduced pressure stream to a second heat exchange zone associated with the first separation zone and configured to vaporize liquid in the reduced pressure stream and provide a vaporized propylene stream, wherein the second heat exchange zone also receives a portion of the overhead stream from the first separation zone; passing the vaporized propylene stream to a second compression zone configured to compress the vaporized propylene stream and provide a re-compressed propylene stream; and, passing the re-compressed propylene stream to the separation vessel. An embodiment of the invention is one, any or all of prior embodiments in this paragraph up through the second embodiment in this paragraph further comprising passing the vapor propylene stream from the separation vessel to the second compression zone. An embodiment of the invention is one, any or all of prior embodiments in this paragraph up through the second embodiment in this paragraph further comprising removing heat from the re-compressed propylene stream before the propylene is passed to the separation vessel. An embodiment of the invention is one, any or all of prior embodiments in this paragraph up through the second embodiment in this paragraph further comprising passing the re-compressed propylene stream to a third heat exchange zone associated with the third separation zone; and, then passing the re-compressed propylene stream from the third heat exchange zone to the separation vessel. An embodiment of the invention is one, any or all of prior embodiments in this paragraph up through the second embodiment in this paragraph further comprising passing the first portion of the compressed propylene overhead stream from the first heat exchange zone to a fractionation column in the second separation zone. An embodiment of the invention is one, any or all of prior embodiments in this paragraph up through the second embodiment in this paragraph further comprising recovering a second portion of the liquid propylene stream as a propylene product stream. An embodiment of the invention is one, any or all of prior embodiments in this paragraph up through the second embodiment in this paragraph further comprising passing a third portion of the liquid propylene stream to a fractionation column in the second separation zone. An embodiment of the invention is one, any or all of prior embodiments in this paragraph up through the second embodiment in this paragraph wherein the first separation zone comprises a fractionation column, and wherein the second separation zone comprises a fractionation column. An embodiment of the invention is one, any or all of prior embodiments in this paragraph up through the second embodiment in this paragraph further comprising removing heat from the re-compressed propylene stream before the propylene is passed to the separation vessel.

A third embodiment of the invention is a system for separating hydrocarbons and recovering heat comprising a first separation zone comprising a fractionation column configured to receive and separate a stream into an overhead stream and a C3+ bottoms stream; a second separation zone comprising a fractionation column configured to receive and separate the C3+ bottoms stream and provide a propylene overhead stream and a bottoms stream, the bottom stream comprising propane; a first compression zone configured to compress the propylene overhead stream and provide a compressed propylene overhead stream; a heat exchange zone associated with the second separation zone and configured to remove heat from the first portion of the compressed propylene overhead stream; a separation vessel configured to receive and separate a second portion of the compressed propylene overhead stream into a vapor propylene stream and a liquid propylene stream; a valve configured to receive a portion of the liquid propylene stream and provide a reduced pressure stream; a second heat exchange zone, the second heat exchange zone associated with the first separation zone and configured to heat the reduced pressure portion and provide a vaporized propylene stream; a second compression zone configured to compress the reduced pressure stream and the vapor propylene stream and provide a re-compressed propylene stream; and, one or more lines configured to pass the re-compressed propylene stream to the separation vessel. An embodiment of the invention is one, any or all of prior embodiments in this paragraph up through the third embodiment in this paragraph further comprising a third heat exchange zone configured to remove heat from the re-compressed propylene stream, the third heat exchange zone disposed between the separation vessel and the second compression zone.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

The invention claimed is:

1. A process for separating hydrocarbons and recovering heat comprising:
separating a stream comprising C4− hydrocarbons in a first separation zone into an overhead stream and a C3+ bottoms stream;
separating the C3+ bottoms stream in a second separation zone into a propylene overhead stream and a bottoms stream comprising propane;
compressing the propylene overhead stream in a first compression zone configured to provide a compressed propylene overhead stream;
recovering heat from a first portion of the compressed propylene overhead stream in a heat exchange zone associated with the second separation zone;
condensing a second portion of the compressed propylene overhead stream in a separation vessel, the separation vessel providing a propylene vapor stream and a propylene liquid stream;
reducing a pressure of at least a portion of the propylene liquid stream to provide a reduced pressure stream;
recovering heat from the reduced pressure stream in a second heat exchange zone, the second heat exchange zone associated with the first separation zone and being configured to condense a portion of the overhead stream and provide a vaporized propylene stream;
compressing the vaporized propylene stream in a second compression zone configured to provide a re-compressed propylene stream; and,
mixing the re-compressed propylene stream with the second portion of the compressed propylene overhead stream in the separation vessel.

2. The process of claim 1 further comprising:
compressing the propylene vapor stream from the separation vessel in the second compression zone.

3. The process of claim 2 further comprising:
removing heat from the re-compressed propylene stream before the re-compressed propylene stream is mixed with the second portion of the compressed propylene overhead stream in the separation vessel.

4. The process of claim 3 wherein the heat is removed from the re-compressed propylene stream in a third heat exchange zone associated with a third separation zone configured to receive the bottoms stream from the second separation zone.

5. The process of claim 1 further comprising:
separating the first portion of the compressed propylene overhead stream in a fractionation column in the second separation zone.

6. The process of claim 1 further comprising:
recovering a second portion of the propylene liquid stream as a propylene product stream.

7. The process of claim 1 further comprising:
refluxing a third portion of the propylene liquid stream from the separation vessel to a fractionation column in the second separation zone.

8. The process of claim 1 wherein the first separation zone comprises two fractionation columns, and wherein the second separation zone comprises a fractionation column.

9. The process of claim 1 further comprising:
transferring heat from the re-compressed propylene stream to a third separation zone configured to receive the bottoms stream from the second separation zone.

10. A process for separating hydrocarbons and recovering heat comprising:
separating a stream comprising C4− hydrocarbons in a first separation zone configured to separate the stream into an overhead stream and a C3+ bottoms stream;
passing the C3+ bottoms stream to a second separation zone configured to separate the C3+ bottoms stream and provide a propylene overhead stream and a bottoms stream, the bottom stream including propane;
passing the bottoms stream of the second separation zone to a third separation zone;
passing the propylene overhead stream to a first compression zone configured to compress the propylene overhead stream and provide a compressed propylene overhead stream;
passing a first portion of the compressed propylene overhead stream to a heat exchange zone associated with the second separation zone configured to remove heat from the first portion of the compressed propylene overhead stream;
passing a second portion of the compressed propylene overhead stream to a separation vessel configured to allow the second portion of the compressed propylene overhead stream to be cooled and separate into a vapor propylene stream and a liquid propylene stream;
reducing a pressure of at least a portion of the liquid propylene stream to provide a reduced pressure stream, the reduced pressure stream comprising a mixture of liquid and vapor;
passing the reduced pressure stream to a second heat exchange zone associated with the first separation zone and configured to vaporize liquid in the reduced pressure stream and provide a vaporized propylene stream, wherein the second heat exchange zone also receives a portion of the overhead stream from the first separation zone;
passing the vaporized propylene stream to a second compression zone configured to compress the vaporized propylene stream and provide a re-compressed propylene stream; and,
passing the re-compressed propylene stream to the separation vessel.

11. The process of claim 10 further comprising:
passing the vapor propylene stream from the separation vessel to the second compression zone.

12. The process of claim 11 further comprising:
removing heat from the re-compressed propylene stream before the propylene is passed to the separation vessel.

13. The process of claim 12 further comprising:
passing the re-compressed propylene stream to a third heat exchange zone associated with the third separation zone; and,
then passing the re-compressed propylene stream from the third heat exchange zone to the separation vessel.

14. The process of claim 10 further comprising:
passing the first portion of the compressed propylene overhead stream from the first heat exchange zone to a fractionation column in the second separation zone.

15. The process of claim 10 further comprising:
recovering a second portion of the liquid propylene stream as a propylene product stream.

16. The process of claim 10 further comprising:
passing a third portion of the liquid propylene stream to a fractionation column in the second separation zone.

17. The process of claim 10 wherein the first separation zone comprises a fractionation column, and wherein the second separation zone comprises a fractionation column.

18. The process of claim 10 further comprising:
removing heat from the re-compressed propylene stream before the propylene is passed to the separation vessel.

* * * * *